United States Patent [19]

McFall

[11] Patent Number: 5,567,260
[45] Date of Patent: Oct. 22, 1996

[54] METHOD FOR ATTACHING A WEB OF MATERIAL TO THE SIDE EDGES OF AN ABSORBENT ARTICLE

[75] Inventor: Ronald R. McFall, Hamilton, Ohio

[73] Assignee: The Procter & Gamble Company, Cincinnati, Ohio

[21] Appl. No.: 501,515

[22] Filed: Jul. 12, 1995

Related U.S. Application Data

[63] Continuation of Ser. No. 293,770, Aug. 19, 1994, abandoned, which is a continuation of Ser. No. 83,428, Jun. 28, 1993, abandoned.

[51] Int. Cl.$^6$ .............................. B32B 3/04; B32B 7/14
[52] U.S. Cl. .................... 156/201; 156/202; 156/216; 156/291
[58] Field of Search ................................ 156/164, 201, 156/202, 204, 216, 229, 291, 295; 427/208.6, 285, 288; 604/385.2, 358, 382, 385.1

[56] References Cited

U.S. PATENT DOCUMENTS

| | | | |
|---|---|---|---|
| 3,756,894 | 9/1973 | Shugart | 156/443 |
| 4,960,619 | 10/1990 | Slautterback et al. | 427/288 |
| 4,995,333 | 2/1991 | Keller et al. | 156/291 |
| 5,234,422 | 8/1993 | Sneller et al. | 604/385.2 |
| 5,342,647 | 8/1994 | Heindel et al. | |

FOREIGN PATENT DOCUMENTS

| | | |
|---|---|---|
| 868842 | 7/1978 | Belgium. |
| WO93/12747 | 7/1993 | WIPO. |

*Primary Examiner*—Michael W. Ball
*Assistant Examiner*—Richard Crispino
*Attorney, Agent, or Firm*—Edward J. Milbrada; Jeffrey V. Bamber; Steven W. Miller

[57] ABSTRACT

A method is disclosed for attaching an elastomeric film laminate web to the longitudinal side edges of an absorbent article such as a sanitary napkin. The method involves using a system of different adhesive applying mechanisms (that is, glue guns) and different applications of adhesive in a spiral pattern to provide precise control over the pattern and the amount of adhesive applied to bond the web of material to the absorbent article. The method comprises applying a narrow spiral of adhesive to a first portion of the width of the web that is adjacent a first edge of the web; bringing the first portion of the web into contact with a first face of the sanitary napkin so that the remaining portion of the web extends outward beyond the edge of the sanitary napkin; applying a second narrow spiral of adhesive to a second portion of the width of the web adjacent the second edge of the same; folding the second portion of the width of the web onto the second face of the sanitary napkin to wrap the edge of the sanitary napkin; and securing the wrapped web to the sanitary napkin.

12 Claims, 3 Drawing Sheets

METHOD FOR ATTACHING A WEB OF MATERIAL TO THE SIDE EDGES OF AN ABSORBENT ARTICLE

This is a continuation of application Ser. No. 08/293,770, filed on Aug. 19, 1994, now abandoned which is a continuation of application Ser. No. 08/083,428, filed on Jun. 28, 1993, now abandoned.

FIELD OF THE INVENTION

The present invention is directed to a method of making an absorbent article. More particularly, the present invention is directed to a method of attaching a web of elastic material to the side edges of an absorbent article as part of the process of making an elasticated sanitary napkin.

BACKGROUND OF THE INVENTION

A wide variety of types of structures for disposable absorbent articles used to collect body fluids are known in the art. Commercially available absorbent articles include diapers, adult incontinence products, catamenials and bandages. Disposable products of this type comprise components for receiving, absorbing and retaining fluids. Typically, such articles include a liquid permeable topsheet, an absorbent core, and a liquid impermeable backsheet.

Disposable absorbent articles have previously been provided with elastic members to improve the side leakage performance of such products. For example, U.S. Pat. No. 3,860,003, issued to Buell on Jan. 14, 1975, discloses elasticized disposable absorbent articles wherein an elastic member is positioned in the side flap of the product between the topsheet and the backsheet. The side flap is gathered by the elastic member such that a boat-like configuration for the pad is presented and the side flaps form a barrier along the edges of the product.

An alternative way of providing an absorbent article with an elasticized side flap is to wrap a web of elasticated material, such as an elastomeric film laminate on the longitudinal side edges of the article. The elastomeric film laminate preferably comprises a soft outer coverstock layer so that the portion of the side flap that comes in contact with the wearer during use will be comfortable. A sanitary napkin having an elasticized side flap provided in this manner is described in U.S. Pat. No. 5,234,422. (See also the disclosure of European Patent Application Publication No. 0 534 488 A1, published in the name of Menard, et al., on Mar. 31, 1993.)

Various methods for attaching a web of an elasticized material such as an elastomeric film laminate to the side edges of an absorbent article for this purpose can be attempted. One suitable way for attaching the elastomeric film laminate along the longitudinal side edges of the article is by the use of adhesives. The adhesives can be applied in a variety of forms, including lines, beads, sprays, and spirals. Spirals are preferred because they can be applied in a relatively well defined strip of adhesive, and because the distance between the spirals can be spread out along the length of the strip so that less adhesive is used than if the adhesive were simply sprayed along the entire length of the strip.

One approach for applying adhesive in a spiral pattern to attach such a component or web to an absorbent article would be to apply the adhesive once to one side of the web and then to fold the web around the longituidnal side edge of the absorbent article attaching half of the web to the side of the absorbent article that will face the wearer's garment during wear and the other half to the side that will face the wearer's body during wear. Alternatively, the adhesive can be applied to the edges of the absorbent article on both faces of the absorbent article and the web can then be wrapped around and secured to the edges of the absorbent article.

Several problems arise in attempting to attach a web of material to the side edge of an absorbent article in such a manner, particularly when an adhesive application is used to attach the web. First, the adhesive has to be applied very close to the edges of the web of material so that the edges of the web of material will be bonded to the absorbent article. The formation of unbonded edges of the web of material may result in the web of material having a tendency to fold back and give the article an unsightly appearance. The need to apply adhesive close to the edges of the web of material, however, must be balanced against the problems caused when adhesive extends beyond the edges of the web of material. If the adhesive is sprayed beyond the edges of the web of material, the adhesive may be sprayed on the equipment used for assembling the sanitary napkin. In addition, spraying the adhesive beyond the edges of the web of material may cause the undesirable result of the adhesive being sprayed on a portion of the sanitary napkin that comes into contact with the consumer's skin, possibly causing these portions of the absorbent article to stick to the wearer's skin.

Other problems that arise are caused by a tradeoff that exists between the ability to apply adhesive close to both edges of the web of material and the strength of the adhesive bond that can be formed using the adhesive. For example, if it is necessary to create a stronger bond with the web of material, conventional processes which use a single application of adhesive to the web require sacrifices in the ability to apply adhesive near both edges of the web of material. For instance, when adhesive is applied in a spiral pattern, the amount of air pressure employed by the adhesive applying mechanism can be adjusted upwardly or downwardly while the adhesive flow rate remains the same. A reduction in the air pressure provides a smaller spiral pattern having more precisely defined edges. The smaller, more concentrated pattern of adhesive forms a stronger bond between the web of material and the absorbent article where the adhesive has been applied. However, when a single application of adhesive is used to coat the web of material, the smaller pattern results in a decrease in the ability to simultaneously apply adhesive close to both edges of the web of material. An increase in the amount of air pressure, on the other hand, results in a wider application of adhesive being applied to the web of material, which can more nearly approach both edges of the web of material. The increase in the amount of air pressure, however, results in a loss in control over the location of the edge of the application of adhesive. The increase in air pressure also results in a less concentrated adhesive application and, thus, a weaker bond with the web of material.

In addition, attaching the web of material to the edge of the absorbent article using a single application of adhesive provides no mechanism for control over the amount of adhesive applied when there are material variations which require different amounts of adhesive in order to form a secure bond with the web of material. For instance, there may be variations (such as normal manufacturing variations) in any of the materials associated with attaching the web to the absorbent article. The material variations can, for example, occur in the topsheet material, the web of material, and the adhesive used to attach the two. Any of these material variations may require a greater amount of adhesive to be applied to the web of material to form a secure bond with the web of material. There is no way to compensate for this using a single application of adhesive since, as noted above, concentrating the adhesive results in a reduction in the ability to apply adhesive near both edges of the web of material.

Thus, a need exists for improvements in the ability to control the application of adhesive materials to the webs that are to be attached to the side edges of an absorbent article. A need also exists for improvements in the usual methods for applying adhesives that will eliminate the tradeoff that exists between the ability to simultaneously apply adhesive close to both edges of the web of material and the strength of the adhesive bond that can be formed by the adhesive application. Further, a need exists for a method that provides control over the amount of adhesive that can be applied to secure a web of material to an absorbent article when there are variations in the materials used in the process.

It is, therefore, an object of the present invention to provide an improved process for attaching a web of material to the side edges of an absorbent article. In particular, it is an object of the present invention to provide improved control of the pattern of application of adhesive used to attach such a web to an absorbent article.

It is another object of the present invention to provide a process for applying adhesive close to both edges of a web of material which is not accompanied by a reduction in the strength of the bond formed between the web of material and the absorbent article to which it is attached.

It is still another object of the present invention to provide a process for applying adhesive close to the edge of a web of material that has a mechanism for controlling the amount of adhesive applied when there are variations in the raw materials used in the process which require different amounts of adhesive to be applied in order to form a secure bond with the web of material.

These and other objects of the present invention will be more readily apparent when considered in reference to the following description and when taken in conjunction with the accompanying drawings.

SUMMARY OF THE INVENTION

The present invention provides a method for attaching a web of material, such as an elastomeric film laminate, to the longitudinal side edges of an absorbent article so that a web of elastomeric film laminate wraps around each side edge of the absorbent article.

The method essentially involves using a system of different adhesive applying mechanisms (that is, glue guns) and different applications of adhesive to provide very precise control over the pattern and the amount of adhesive applied to bond the web of material to the absorbent article. The method is particularly useful when the adhesive is applied in a spiral pattern.

The method comprises the steps of:

(a) providing an absorbent article having an edge, a first face, and a second face;

(b) providing a web of elastomeric film laminate which has a width;

(c) applying adhesive to a first portion of the width of the web of elastomeric film laminate along an edge of the same;

(d) bringing the first portion of the width of the web of elastomeric film laminate into contact with the first face of the absorbent article so that the remaining portion of the width of the web of elastomeric film laminate comprises a second portion, and the second portion of the width of the elastomeric film laminate extends outward beyond the edge of said absorbent article;

(e) applying adhesive to the second portion of the width of the elastomeric film laminate along the edge of the same;

(f) folding the second portion of the width of the elastomeric film laminate onto the second face of the absorbent article to wrap the edge of said absorbent article;

(g) securing the wrapped web of elastomeric film laminate to the absorbent article.

The key to the present invention is to use more than one separate adhesive application in order to allow each application to be controlled independently. This permits the use of applications of adhesive in a smaller or narrower pattern than if the width of the entire web was coated by a single adhesive application. The provision of the separate narrower applications of spirals of adhesive provides more control over the distance between the outer edge of the pattern of adhesive applied to the film laminate and the edge of the film laminate. (The increased control over this distance may also be referred to as more precise "edge definition" of the applications of adhesive.) The more precise edge definition permits the adhesive to be applied very close to the edge of the web of material without applying adhesive beyond the edge of the web.

In addition, the method eliminates the tradeoff between the ability to apply adhesive close to both edges of the web of material and the strength of the adhesive bond that can be formed using the adhesive. This is achieved by providing adhesive applications that can be controlled independently to provide both the ability to apply the adhesive close to the edge of the web and to apply adhesive in sufficient amounts to form a strong bond between the web of material and the absorbent article. The method also provides a mechanism for control over the amount of adhesive applied when there are variations in the raw materials used in the process which require different amounts of adhesive in order to form a secure bond with the web of material. This is achieved by providing adhesive applications that can be controlled independently depending on the materials that are to be bonded.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings, and in which:

DETAILED DESCRIPTION OF THE INVENTION

1. Description of the Representative Absorbent Article

Figure 1:
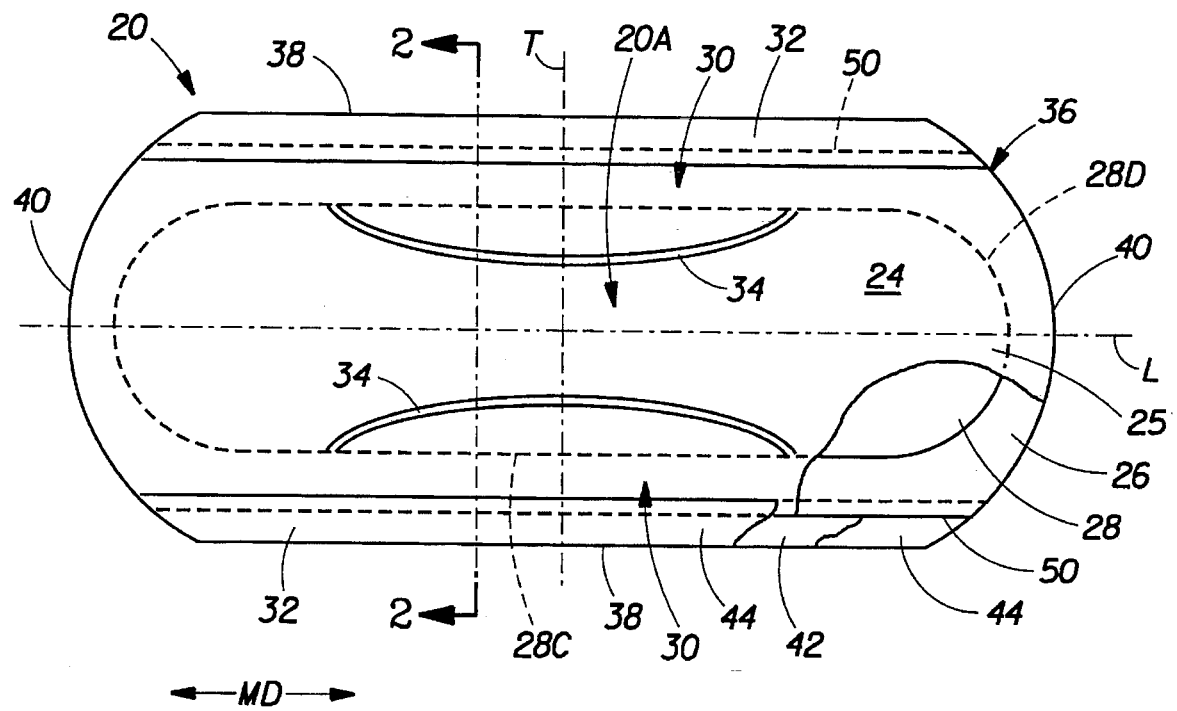
FIG. 1 is a plan view of a representative sanitary napkin that can have a web of material attached to its longitudinal side edges by the method of the present invention.

FIG. 1 is a plan view of a preferred sanitary napkin 20 that can have a web of material attached to its longitudinal side edges by the method of the present invention.

The sanitary napkin is shown in its flat-out state with portions of its structure being cut-away to more clearly show the construction of the sanitary napkin 20. The sanitary napkin is shown with the portion of the sanitary napkin 20 which faces the wearer, body surface 20A, facing the viewer. As shown in FIG. 1, the sanitary napkin 20 comprises a liquid pervious topsheet 24, a liquid impervious backsheet 26 joined with the topsheet 24, an absorbent core 28 positioned between the topsheet 24 and the backsheet 26, a side flap or ("side margin") 30 extending outwardly from and along the side edges 28C of the absorbent core 28, elastic members 32 joined to the side flaps 30, and embossed channels 34.

FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form not only the side flaps 30 but also portions of the periphery 36 of the sanitary napkin 20. The periphery 36 defines the outer perimeter or, in other words, the edges of the sanitary napkin 20. The periphery 36 comprises the longitudinal side edges 38 and the end edges 40. (It should be understood that while the absorbent article is shown in the form of a sanitary napkin, the method described herein can also be used to make other types of absorbent articles such as panty liners, incontinence pads, and the like.)

The sanitary napkin 20 has a longitudinal centerline and a transverse centerline, designated L and T, respectively, in FIG. 1. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

These terms may also be used interchangably with the terms machine direction and cross-machine direction (abbreviated "MD" and "CD", respectively). The term "machine direction" refers to the direction of product flow through the process of making the sanitary napkin. The sanitary napkin preferably goes through the process with its longitudinal centerline oriented in the machine direction. The term "cross-machine direction" refers to a direction perpendicular to the direction of product flow in the process of making the sanitary napkin.

Figure 2:
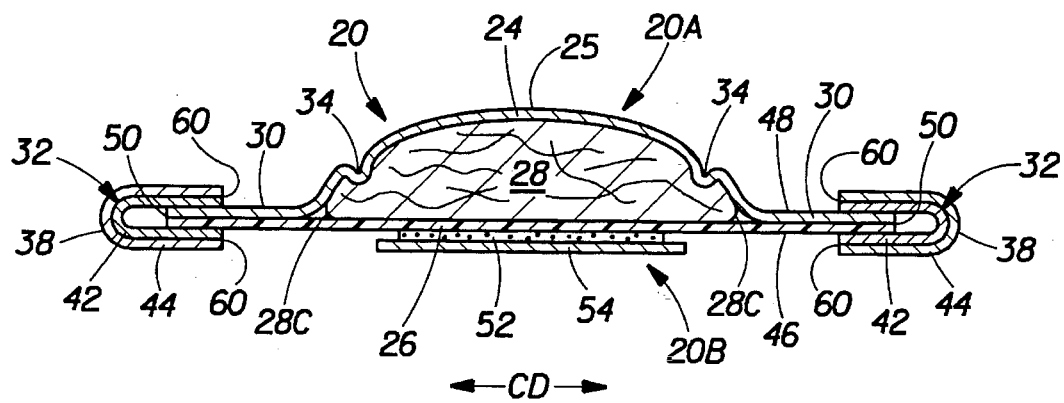
FIG. 2 is a cross-sectional view of the sanitary napkin taken along line 2—2 of FIG. 1.

FIG. 2 is a cross-sectional view of the sanitary napkin 20 taken along section line 2—2 of FIG. 1. FIG. 2 shows the topsheet 24 and the backsheet 26 extending laterally across the entire cross-section to form each side flap 30. The absorbent core 28 is generally shown in FIG. 2 as being thicker in the center than at its edges (i.e., profiled) and positioned between the topsheet 24 and the backsheet 26 such that the topsheet 24 and the backsheet 26 encase the absorbent core 28. The embossed channels 34 are shown in FIG. 2 as being a region of the sanitary napkin 20 wherein preferably both the topsheet 24 and the absorbent core 28 are compressed.

FIG. 2 also shows that the garment surface 20B of the sanitary napkin 20 is provided with a fastener, such as a pressure sensitive adhesive fastener 52 for attaching the sanitary napkin 20 to the wearer's panties. The adhesive fastener 52 is preferably covered with a release paper 54 to keep the adhesive from sticking to surfaces other than the panties prior to use of the sanitary napkin.

FIG. 2 shows that the elastic members 32 comprise an elastomeric laminate comprising an elastomeric layer 42 and a nonwoven coverstock layer 44. The elastic members 32 each have a pair of longitudinal edges 60. One portion of the elastic member 32 is secured to the outer surface 46 of the side flap 30 (i.e., the backsheet 26) with the other portion secured to the inner surface 48 of the side flap 30 (i.e., the topsheet 24). The elastic member 32 has been folded about the distal edge 50 of the side flap 30 such that the elastic member 32 forms the longitudinal edge 38 of the sanitary napkin 20. The contraction of the elastic member 32 will cause the side flaps 30 to stand-up (fold upwardly toward the topsheet 24) to form a wall that acts as a lateral barrier to the flow of menstrual fluids.

The sanitary napkin 20 is, thus, provided with an elasticized side flap by operatively associating an elastic member on both the upper surface and the lower surface of the side flap. Since the coverstock layer is on the outside of the product, the sanitary napkin is provided with soft side edges which contact the wearer during use. In addition, the elastomeric laminate provides relatively low tension that, while being sufficient for raising the side flaps of the product to be a barrier against lateral leakage, also maintains the product in a shape which discourages fluid run-off or leakage at the ends of the pad as well as providing a bunching benefit. The sanitary napkin 20 shown in FIGS. 1 and 2 is described in greater detail in the above mentioned U.S. Pat. No. 5,344, 222 which is incorporated by reference herein.

2. Description of the Method for Making a Web of Elastomeric Material and Attaching the Web of Elastomeric Material to the Longitudinal Side Edges of the Sanitary Napkin FIG. 3 is a schematic perspective view of the overall process and apparatus for forming an elastomeric film laminate, cutting the laminate, and attaching the same to the longitudinal side edges of a sanitary napkin.

The overall apparatus 70 for making the elastomeric film laminate and attaching the web of elastomeric material to the longitudinal side edges of the sanitary napkin comprises an apparatus for making the elastomeric film laminate, designated by reference number 80, and an apparatus for attaching the elasomeric film laminate to the longitudinal side edges of the sanitary napkin, designated by reference number 100.

The apparatus for making the elastomeric film laminate 80 comprises: a conventional elastomeric film supply source, such as a roll of elastomeric film (not shown); a conventional coverstock (or nonwoven) material supply source, such as a roll of nonwoven material (not shown); a laminate combining means, such as a laminate adhesive applying mechanism (or laminate glue gun) 82; a pair of chilled combining rolls 84 and 86; a slitter 88; a slitter anvil roll 90; additional rolls 92 and 94; and, a pair of elastomeric film laminate separating idler rolls 96 and 98.

Figure 3:
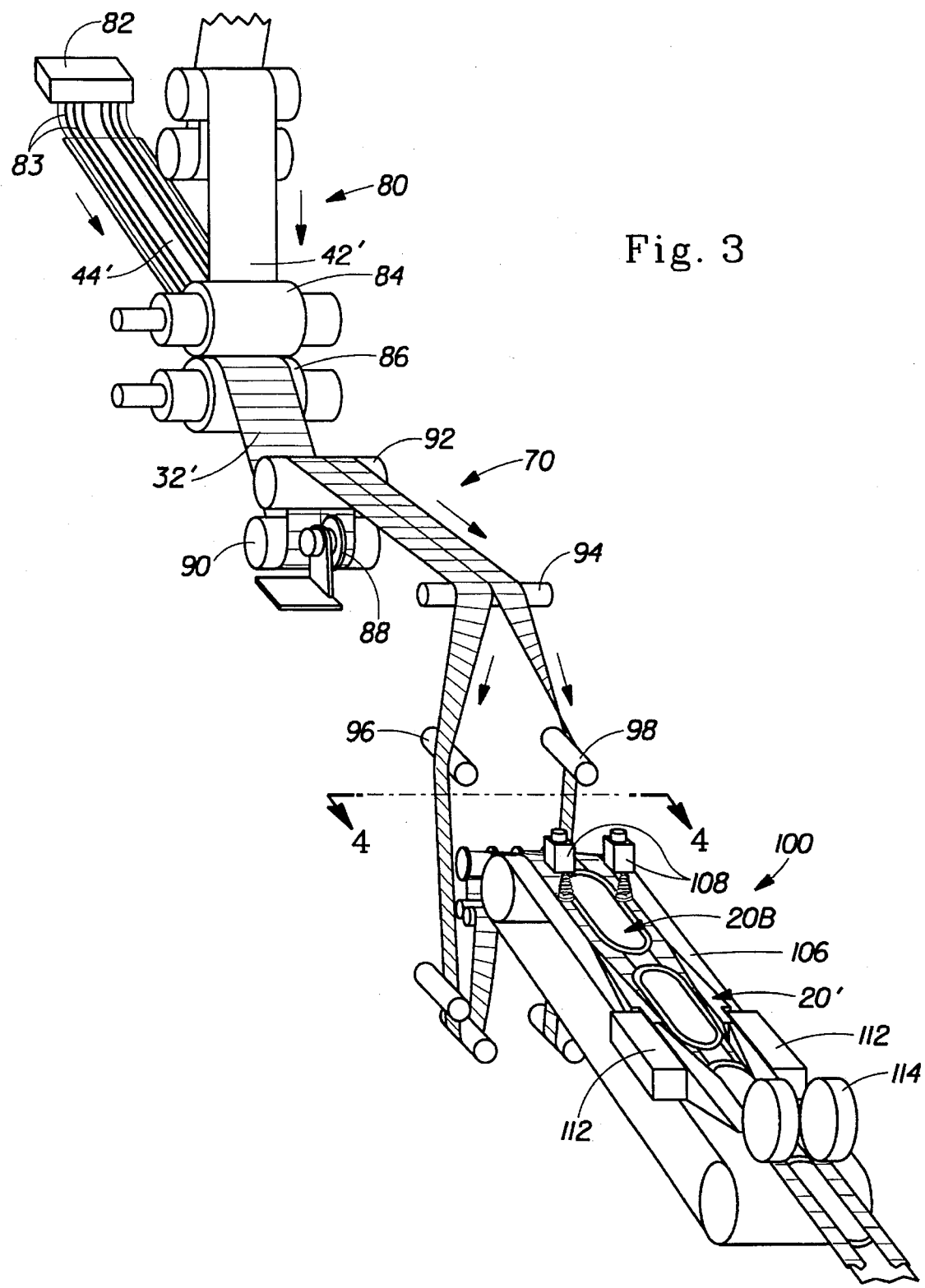
FIG. 3 is a schematic perspective view of the overall process and apparatus for forming an elastomeric film laminate, cutting the laminate, and attaching the same to the longitudinal side edges of a sanitary napkin.

The materials used to from the elastomeric film laminate 32 are brought into the process from the upper left hand corner of FIG. 3. The elastomeric film laminate is comprised of two materials. The first material is an Exxon 500 elastomeric film available from Exxon Chemical Company of Lake Zurich, Ill. This is a live elastic material, meaning it is much like a rubber band when it is brought into the process unlike some elastic diaper waistband materials which have to be heat activated. The second material is a hydroentangled polypropylene fiber nonwoven material. The hydroentangled polypropylene material is applied to the elastomeric film so that the polypropylene material will be affixed on top of the elastomeric film in the finished product.

FIG. 3 shows that the elastomeric film and the nonwoven material are supplied to the process in the form of continuous webs, 42' and 44', respectively. The web of elastomeric film 42' and the nonwoven web 44' are secured together to form the above-described elastomeric film laminate in an operation that occurs before the elastomeric laminate film reaches the apparatus shown in FIG. 4. In this laminate-forming operation, the web of elastomeric film 42' is fed in at a different feed rate than the web of nonwoven material 44'. The web of elastomeric film 42' is fed in approximately 40% to 50% slower than the web of nonwoven material 44' so that it is stretched more than the nonwoven material before it is combined with the nonwoven material. The web of nonwoven material 44' is secured to web of the elastomeric film 42' by beads of hot glue 83 which are applied from a slot glue gun 82. The beads of glue 83 are applied directly to the nonwoven material 44' rather than to the elastomeric film to avoid the problem of the glue melting through the elastomeric film.

The elastomeric film and the nonwoven material are then combined (i.e., secured), and the glue is cooled (or "chilled") to control the spreading of the adhesive. This is done by passing the laminate through a cooling mechanism, such as the pair of "chilled combining rolls" (or "chill rolls") designated 84 and 86 in FIG. 3. The chilled rolls preferably comprise hollow metal rolls that are filled with a coolant, such as Glycol. The chill rolls 84 and 86 have a mechanism for circulating the coolant through the interiors of the rolls. The chill rolls are preferably chilled to a temperature of between about 0° F. and −20° F. The cooling of the glue beads is particularly important for several reasons. The cooling of the glue beads prevents the glue beads from spreading beyond the edges of the web of elastomeric film laminate. This prevents buildup of glue on the equipment used to make the absorbent article. The cooling of the glue beads also reduces the tackiness of the adhesive. This is important because even if the adhesive spreads beyond the edges of the elastomeric film laminate and is exposed to the equipment used to make the absorbent article, the process of the present invention will not be subject to the problem of the various webs adhering to the equipment and wrapping around the equipment, causing the manufacturing line to shut down.

After the web of elastomeric film 42' and the nonwoven web 44' are combined, the web of elastomeric film laminate 32' formed in the process is kept under tension by stretching the same between about 5% to about 15%, preferably about 10%, through the rest of the process (that is until after it is attached to the longitudinal side edges of the absorbent article).

The web of elastomeric film laminate 32', once formed, is then slit into two separate webs. The web is slit between two of the glue beads with a slitter 88 which is in the form of a rotating disk or rotating knife blade. The two separate webs are then moved aside and fed back underneath the line where the glue is then applied to adhere the elastomeric film laminate to the longitudinal side edges of the sanitary napkin.

Figure 4:
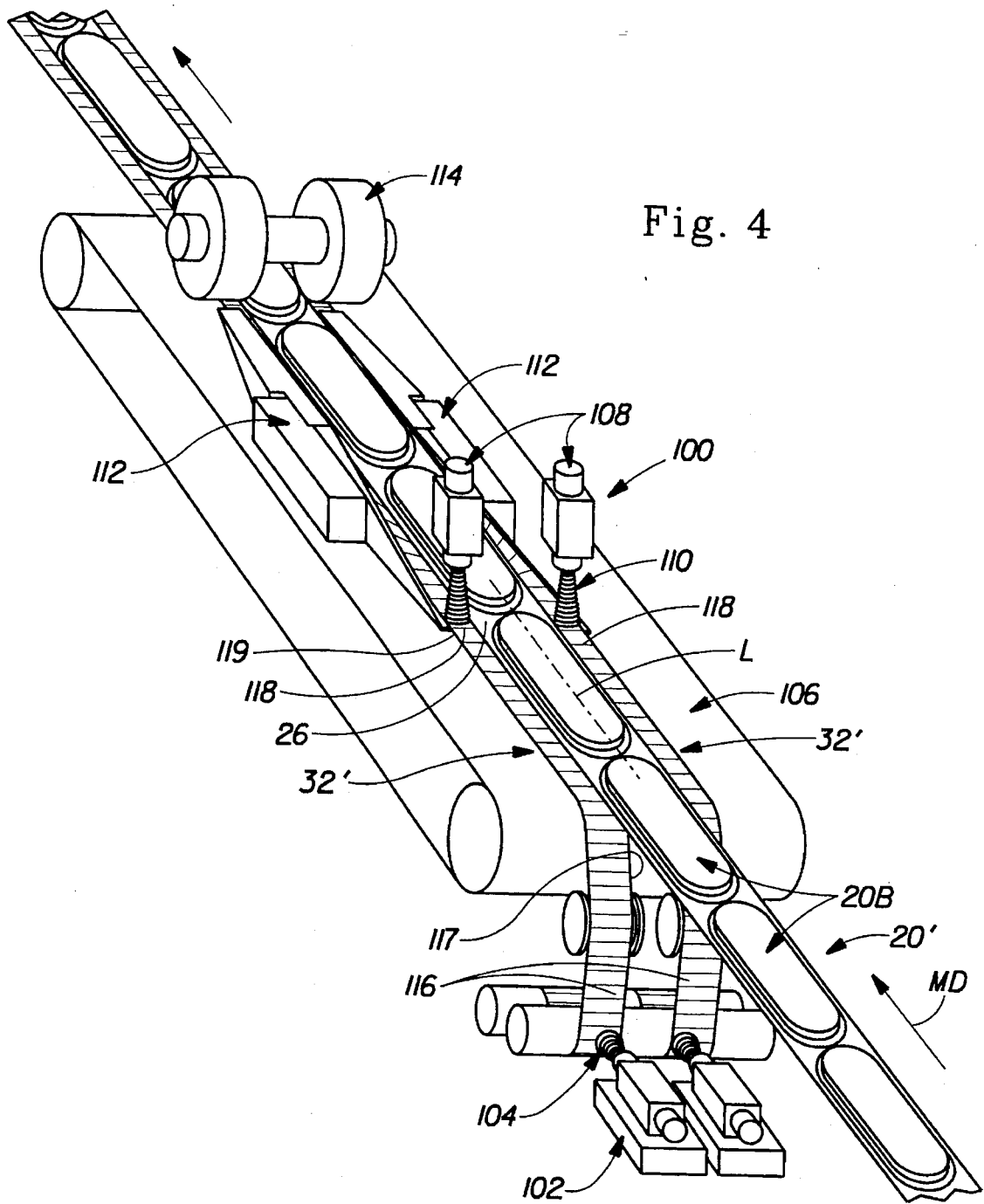
FIG. 4 is a schematic perspective view of the portion of the process in which the elastomeric film laminate is added to the longitudinal side edges of the sanitary napkin.

FIG. 4 is a schematic perspective view of the process in which the elastomeric film laminate is added to the longitudinal side edges of the sanitary napkin.

The overall apparatus for attaching the web of elastomeric material to the longitudinal side edges of the sanitary napkin (elastic attaching apparatus) is designated by reference number 100. The elastic attaching apparatus 100 comprises: a first pair of adhesive applying mechanisms, such as lower glue guns 102, for applying a first spiral pattern 104 of adhesive to each separate web 32' of elastomeric film laminate; a folding conveyor 106 which carries the web 20' of sanitary napkins that are ready to have elastomeric film laminate attached to their longitudinal side edges; a second pair of adhesive applying mechanisms, such as upper glue guns 108, for applying a second spiral pattern 110 of adhesive to the webs 32' of elastomeric film laminate; a pair of folding plows 112; and a pair of combining rolls 114.

The sanitary napkins 20 to which the elastomeric film laminate is to be attached come into the process in the form of a continuous web 20' shown in the lower right hand corner of FIG. 4 with the individual napkins having their garment sides 20B facing upward. The webs 32' of elastomeric film laminate material are also shown as being introduced into the process in the lower right hand corner of FIG. 4. The webs 32' of elastomeric film laminate material are brought into the process from beneath the web 20' of sanitary napkins.

FIG. 4 shows that the first application of adhesive is applied by the lower glue guns 102. The webs of elastomeric film laminate 32' to which the adhesive is applied may, by way of example, be about 15 mm wide. The first application of adhesive is in a spiral pattern 104 that is, in such an example, about 6 to 7 millimeters wide. Suitable methods and apparatus for applying adhesive in a spiral pattern are illustrated in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. 4,842,666 issued to Werenicz on Jun. 27, 1989. Each of these patents is incorporated by reference herein.

The first application of adhesive is applied to a first portion of each separate elastomeric film laminate web 32'. FIG. 4, however, is a somewhat over-simplified schematic drawing which shows the adhesive as being applied across the entire width of the elastomeric film laminate webs 32'. The adhesive is actually only applied to a portion of the width of the elastomeric film laminate. In the embodiment of the process shown in FIG. 4 of the drawings, this first portion is at least a portion of the half of each web, shown as 116, that is closest to the longitudinal centerline, L, of the sanitary napkin. The first portion 116 of the elastomeric film laminate webs will be attached to a first face of the sanitary napkin (such as the topsheet side of the sanitary napkin). FIG. 4 shows that since the product is made upside down, this first portion 116 of the elastomeric film laminate webs will be attached to the side of the sanitary napkins that is facing down on the conveyor.

The first application of adhesive is applied to only a portion of the width of each of the elastomeric film laminate webs to control the edge definition of the glue pattern. The first application can be applied very close to the edge of the first portion (that is, close to the first or inside edges 117). The smaller spirals have less variance in the size and boundaries of the pattern they define (i.e., a smaller standard deviation), and, thus, provide greater control of the edge of the spiral pattern. Before the development of the process of the present invention, the inventor of the present process was only able to apply adhesive within an average of about 5 mm from the edges of each separate web of elastomeric film laminate, with a standard deviation of over 1 (e.g., about 1.2) using a single adhesive application across the entire width of each web. The process of the present invention permits the adhesive to be applied within an average of about 2 mm from the edge of the elastomeric film laminate, with a standard deviation of about 0.5.

The first portion 116 of the webs of elastomeric film laminate 32' is then brought into contact with the inner surface of the side flap (i.e., the topsheet side). The first portion 116 of the elastomeric film laminate 32' may, but need not, have sufficient pressure applied to it at this point to actually attach the first portion 116 to the topsheet side of the sanitary napkin. Preferably, at least some pressure is applied by the folding conveyor 106 to hold the first portion 116 of the webs of elastomeric film laminate 32' to the topsheet side of the web of sanitary napkins.

The webs of elastomeric film laminate material are brought into alignment with the longitudinal side edges of the web of sanitary napkins, where a second application of adhesive occurs. The second application of adhesive is applied by the upper glue guns 108. The second application is applied to the second portion of the width of the webs of elastomeric film laminate very close to the second or outside edges 119 of the webs. The second spiral application of adhesive 110 is also preferably about 6 to 7 mm wide. The second spiral 110 can be applied only to the second portion 118 of the width of each of the webs of elastomeric film laminate. Alternatively, the second application of adhesive 110 can overlap onto a portion of the backsheet 26 that will be covered by the second portion 118 of the width of the elastomeric film laminate. (The second portion 118 of the width of the elastomeric film laminate web is the portion of the webs that will be attached to the backsheet of the sanitary napkins in the embodiment shown. )

The separate second application of adhesive 110 permits the adhesive to be applied closer to the edges of the webs of elastomeric film laminate 32'. The separate adhesive applications also eliminate any tradeoffs between the ability to apply adhesive close to both edges of the webs and the strength of the bond formed between the webs and the sanitary napkin. The second application of adhesive provides the additional advantage that the two adhesive applications can be controlled separately in the event that there is a variation in the materials associated with attaching the webs to the sanitary napkin. Additional adhesive applying mechanisms can also be added for this purpose. The multiple adhesive applying mechanisms allow the concentration of the adhesive applied to the elastomeric film laminate to be controlled depending on the characteristics of materials used in the process. This is particularly useful in the event a more concentrated application of adhesive is needed to form a secure bond between the webs and the sanitary napkin.

The webs of elastomeric film laminate 32' are attached to the web of sanitary napkins in the following manner. The laminate is first brought adjacent to the topsheet side of the web of sanitary napkins. The laminate is then folded over onto the backsheet side by a pair of folding plows 112. When the topsheet and backsheet sides of the webs are folded into position, a pair of combining rolls 114 with set clearances between them apply pressure to permanently affix the elastomeric film laminate webs to the edges of the sanitary napkins.

Once combined, the webs comprising the elastomeric film laminate are then allowed to relax. This causes the side flaps to stand up and form side barriers. In addition, when the elastomeric film relaxes, since it was under tension, it retracts and pulls on the nonwoven material. This gives the elastomeric film laminate a ruffled appearance.

Numerous alternative embodiments of the process and apparatus of the present invention are possible. In alternative embodiments, the steps of the process can be performed in many other orders and in many other manners, all of which are within the scope of the present invention. For instance, the material attached to the side edges of the sanitary napkins can be a different type of elastic material than the elastomeric film laminate described above. In addition, the order in which the material is attached to the edges of the sanitary napkin can be reversed so that it is attached to the backsheet side of the sanitary napkin and then to the topsheet side.

In still other alternative embodiments, rather than folding a single web of material around the edges of the sanitary napkin and attaching a portion of the web of material to the topsheet side and another portion of the web to the backsheet side of the napkin, two or more separate webs of material can be attached so that at least one is attached to each side of the sanitary napkin. In yet other alternative embodiments, the material can be attached to the end edges of an absorbent article rather than (or in addition to), the longitudinal side edges of the article. In other embodiments, instead of applying the adhesive in a spiral pattern, at least one of the applications of adhesive can be applied in a spray pattern (or other suitable pattern).

The present invention, in fact, can be used in any case where it is desired to create a bond between two overlapping materials. This is particularly the case where separate or overlapping applications of adhesive supplied by multiple adhesive applying mechanisms are beneficial. The multiple adhesive applying mechanisms can either be aligned along the same axis with relation to the materials to be bonded, or they can be offset on different axes. In the latter case, the adhesive applying mechanisms can be arranged to apply adhesive in separate offset patterns, or in overlapping patterns, depending on the width of each pattern of application.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of attaching a web of material to an edge of an absorbent article comprising the steps of:

(a) providing an absorbent article having an edge, a first face, and a second face;

(b) providing a web of material, having a first edge, a second edge, and a width;

(c) applying adhesive to a first portion of the width of said web of material adjacent the first edge of said web of material through a nozzle using a first adhesive application mechanism;

(d) bringing said first portion of the width of the web of material into contact with the first face of the absorbent article so that the remaining portion of the width of the web of material comprises a second portion, and said second portion of the width of the web of material extends outward beyond the edge of said absorbent article;

(e) applying adhesive to a second portion of said web of material and a portion of the second face of the absorbent article adjacent the edge of said absorbent article through a nozzle using a second adhesive application mechanism;

(f) folding the second portion of the width of the web of material onto said second face of the absorbent article to wrap the edge of said absorbent article;

(g) securing the wrapped web of material to the absorbent article.

2. The method of attaching a web of material to an edge of an absorbent article of claim 1 wherein at least one of said applications of adhesive comprises a spiral pattern of adhesive.

3. The method of attaching a web of material to an edge of an absorbent article of claims 1 or 2 wherein said web of material is elastomeric.

4. The method of attaching a web of material to an edge of an absorbent article of claim 3 wherein said web of material comprises an elastomeric film laminate.

5. A method of attaching a web of material to an edge of an absorbent article so that the web of material wraps the edge of said absorbent article, said method comprising the steps of:

(a) providing an absorbent article having an edge, a first face, and a second face;

(b) providing a web of material, said web of material having a first edge, a second edge, and a width;

(c) applying a first application of adhesive to a first portion of the width of said web of material adjacent the first edge of said web of material;

(d) applying a second application of adhesive to a second portion of the width of said web of material and a portion of the second face of said absorbent article adjacent the edge of said absorbent article;

(e) placing said first portion of said web of material adjacent the edge of said absorbent article so that it overlaps onto said first face of said absorbent article, and folding said second portion of the width of said web of material onto said second face of said absorbent article to wrap said edge of said absorbent article;

(f) securing said wrapped web of material to said absorbent article.

6. The method of attaching a web of material to an edge of an absorbent article of claim 5 wherein at least one of said applications of adhesive comprises a spiral pattern of adhesive.

7. The method of attaching a web of material to an edge of an absorbent article of claims 5 or 6 wherein said web of material is elastomeric.

8. The method of attaching a web of material to an edge of an absorbent article of claim 7 wherein said web of material comprises an elastomeric film laminate.

9. A method of attaching a web of elastomeric material to a longitudinal side edge of an absorbent article so that said elastomeric material wraps said longitudinal side edge of said absorbent article, said method comprising the steps of:

(a) providing an absorbent article having a pair of longitudinal side edges, a first face, and a second face;

(b) providing a web of elastomeric material, said elastomeric material having a first edge, a second edge, and a width;

(c) applying a first application of adhesive in a first spiral pattern to a first portion of said web of elastomeric material within about two millimeters of the first edge of said web of material, wherein said first spiral pattern has a width that is less than the width of said web of elastomeric material;

(d) bringing said first portion of the width of said web of elastomeric material into contact with said first face of said absorbent article adjacent one of the longitudinal side edges of said absorbent article so that the remaining portion of the width of said web of elastomeric material comprises a second portion and said second portion of the width of said elastomeric material extends outward beyond the longitudinal side edge of said absorbent article;

(e) applying a second application of adhesive in a second spiral pattern to a second portion of the width of said web of elastomeric material and a portion of the second face of said absorbent article, wherein said second spiral pattern has a width that is less than the width of said second portion of said web of elastomeric material;

(f) folding said second portion of the width of said elastomeric material onto said second face of said absorbent article to wrap said longitudinal side edge of said absorbent article;

(g) securing said wrapped web of elastomeric material to said absorbent article.

10. The method of attaching a web of elastomeric material to the edge of an absorbent article of claim 9 wherein said elastomeric material comprises an elastomeric film laminate.

11. The method of claim 10 wherein said method is used to attach a web of elastomeric material to both longitudinal side edges of said absorbent article.

12. The method of attaching a web of elastomeric material to the edge of an absorbent article of claim 11 wherein: said absorbent article comprises a sanitary napkin; the elastomeric film laminate provided in step (b) is under tension so that said elastomeric film laminate is in an extended condition; and, said method further comprises a step (h) of allowing said elastomeric film laminate to contract to provide a stand up barrier to liquids along the longitudinal side edges of said sanitary napkin.

* * * * *